(12) United States Patent
Bakry et al.

(10) Patent No.: US 11,337,897 B1
(45) Date of Patent: May 24, 2022

(54) BIOACTIVE ADHESIVE SYSTEM COMPOSITIONS AND METHODS OF USE

(71) Applicant: King Abdulaziz University, Jeddah (SA)

(72) Inventors: Ahmed Samir Ibrahim Bakry, Jeddah (SA); Mona Aly Abbassy, Jeddah (SA); Rania Bakry, Innsbruck (AT)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/368,882

(22) Filed: Jul. 7, 2021

(51) Int. Cl.
| | |
|---|---|
| *A61K 6/836* | (2020.01) |
| *A61K 6/62* | (2020.01) |
| *A61K 6/889* | (2020.01) |
| *A61C 5/20* | (2017.01) |
| *A61C 5/30* | (2017.01) |
| *A61C 13/15* | (2006.01) |
| *A61K 6/838* | (2020.01) |

(52) U.S. Cl.
CPC ............. *A61K 6/836* (2020.01); *A61C 5/20* (2017.02); *A61C 5/30* (2017.02); *A61C 19/003* (2013.01); *A61K 6/62* (2020.01); *A61K 6/838* (2020.01); *A61K 6/889* (2020.01)

(58) Field of Classification Search
CPC .................................................... A61K 6/836
See application file for complete search history.

(56) References Cited

U.S. PATENT DOCUMENTS

| | | | |
|---|---|---|---|
| 7,090,720 B2 | 8/2006 | Kessler et al. | |
| 9,233,054 B2 | 1/2016 | Rusin et al. | |
| 9,351,908 B2 | 5/2016 | Kalgutkar et al. | |
| 9,517,186 B2 | 12/2016 | Rusin et al. | |
| 10,624,994 B2 | 4/2020 | Bakry et al. | |
| 2015/0094392 A1* | 4/2015 | Takei | A61K 6/75 522/28 |
| 2019/0060523 A1* | 2/2019 | Bakry | A61C 5/00 |
| 2019/0161392 A1 | 5/2019 | Deng et al. | |

OTHER PUBLICATIONS

Ana et al., "Effects of added bioactive glass on the setting and mechanical properties of resin-modified glass ionomer cement", Biomaterials 24 (2003) 3061-3067.

* cited by examiner

*Primary Examiner* — Michael F Pepitone
(74) *Attorney, Agent, or Firm* — WCF IP

(57) ABSTRACT

A bioactive borate glass adhesive system is described for its composition and use in adhering a plurality of dental restorative components onto a tooth surface. The adhesive system comprises silanated borate bioactive glass particles and a biocompatible resin blend. The bioactive adhesive system functions as a non-degradable, permanent adhesive in tooth restoration in the presence of saliva. In addition, the bioactive borate adhesive system may be used for re-mineralization, de-sensitization and self-healing of dentin and enamel by releasing and depositing calcium and phosphate ions onto the exposed and damaged tooth surface.

16 Claims, 5 Drawing Sheets

BIOACTIVE ADHESIVE SYSTEM COMPOSITIONS AND METHODS OF USE

FIELD OF THE INVENTION

The invention relates to compositions of bioactive borate glass adhesive and methods of using such compositions to enhance bonding of dental composite materials on dentin or enamel while re-mineralizing an exposed tooth structure in presence of saliva.

BACKGROUND

Introduction of non-metallic dental composites was a groundbreaking discovery, which expanded dental restorative options for patients by replacing the metal with various types of highly esthetic and durable resinous composites and/or ceramics for dentins and/or for other oral tissue restoration. Recently, bioactive dental composites have been extensively researched for their capacity to release high amounts of calcium and phosphate ions and concomitantly to promote re-mineralization of the exposed enamel and dentin of a tooth. Moreover, the use of the bioactive resin or ceramic as a coating material on the surface of many artificial human body prosthesis proved the efficacy of such composites in the field of orthopedics as well, showing much improved interaction of various artificial prosthesis with human body soft and hard tissues.

Bioactive resin composite is one of the most commonly used dental restorative materials nowadays. Despite the esthetic and enhanced coating functions of the bioactive resin, however, bonding of resins to dental hard tissues is one of the major challenges in the field of dental materials technology. The challenge stems from the difference in compositional structure of the dental hard tissues that are mainly in the form of hydroxyapatite crystals and the resin materials that are composed of catalyst-specific polymeric chains. As such, the inherent chemical differences between the resinous material and the dental enamel or dentin may lead to an integration failure at the interface between the resin and the tooth structure. Moreover, other various acidic, bacterial, thermal, and mechanical challenges that are present in the oral environment, by default, further jeopardize the durability of the resin-tooth interface.

In contrary to resins, ceramics used in dental restoration are mainly composed of the inorganic particles that, in most cases, are inert and highly durable in the oral environment. However, the high stability of ceramics complicates the bonding procedures in the clinical setting. The current clinical approach for ceramic use introduces the same resinous interface issue; to enhance the bonding of the ceramics with enamel or dentin, an effective adhesive material or system is needed for preserving the bonding durability of the inert material on a tooth structure. Thus, there is a need in the art for a new category of dental adhesives with the ability to combine the excellent mechanical properties of the resin materials and the unique durability of bioactive ceramics in challenging oral environment conditions.

SUMMARY OF THE INVENTION

The disclosure provides compositions of bioactive borate glass adhesive that comprise a biocompatible resin blend and silanated bioactive glass particles. The disclosure further includes methods of using such an adhesive system to enhance bonding of dentin restorative components and to re-mineralize an exposed tooth structure in the presence of biofluids (e.g. saliva).

In a particular preferred embodiment, the borate glass particles with bioactive properties are mixed with a blend of resin having adherent mechanical properties to form a bioactive adhesive system. In this embodiment, the borate-based glass particle composition comprises 10-40 mol % $Na_2O$, 20-30 mol % CaO, 1-5 mol % $P_2O_5$, and 30-50 mol % $B_2O_3$, as represented in mole percents based on 100 mol % of the total composition. To manufacture the bioactive borate glass adhesive system, the bioactive borate glass particles are mixed with a resin blend comprising 60-80 wt % of dimethacrylate monomers. In one embodiment, the adhesive system of bioactive borate glass particles is free of phosphoric acid solution. In another embodiment, the adhesive system is substantially free of A1202, $SiO_2$, MgO or mixtures thereof.

In another aspect, the disclosure provides a method to enhance bonding of restorative dental composites and re-mineralization of dental structure by utilizing the adhesive system as described herein. In one embodiment, the adhesive system deposits calcium and phosphate ions to form hydroxyapatite, a putative mineral in enamel and dentin, on the exposed dentin surface when reacted with saliva. As such, by re-mineralizing enamel or dentin lesions, the disclosed bioactive glass formulations are for a long-term, permanent treatment, not only for re-mineralizing but also for de-sensitizing dentin of an exposed tooth.

The adhesive system may be mixed or co-applied with a plurality of restorative materials (e.g. resins or ceramics). Alternatively, the adhesive system may be applied and cured prior to the application of restorative materials to provide the mechanistic surface for the restorative materials to bond on a tooth. The resin blend included in the adhesive system is selected from a material or combinations of materials that are compatible with the dental restoratives that may be subsequently or simultaneously applied with, and is manufactured to ensure good penetration of the dentin surface by light-activated polymerization.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

DETAILED DESCRIPTION

Figure 1:
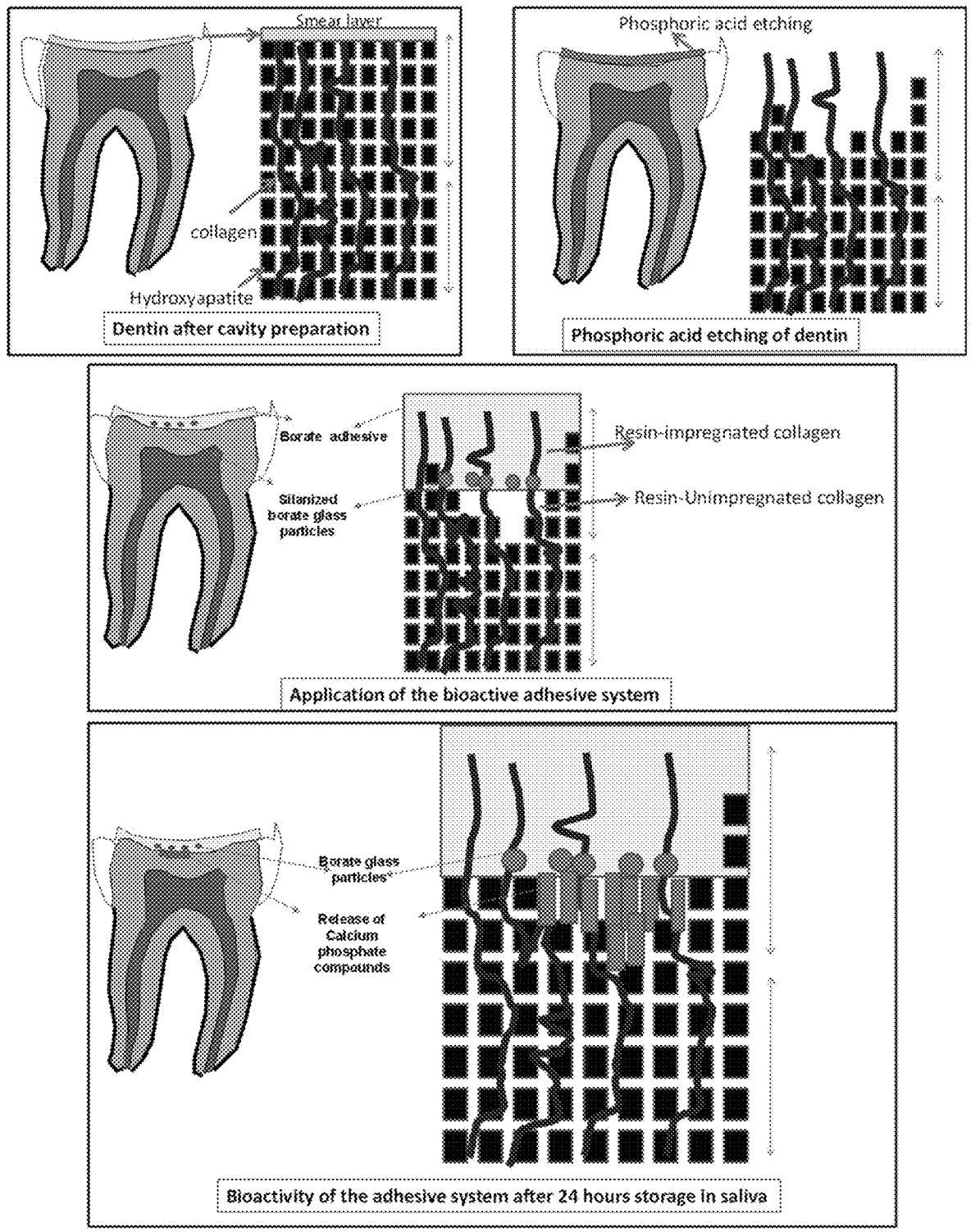
FIG. 1 is an illustration of a method of using a borate glass adhesive system to restore dentin or enamel surface.

The preferred embodiments of the present disclosure are directed toward a bioactive borate glass adhesive system and a method of using such system as an adhesive to enhance bonding of a dental restoration material onto dentin or enamel as well as to re-mineralize an exposed tooth structure by depositing phosphate or calcium ions in the presence of biofluids.

As used herein, the term "bioactive" refers to a material that generates a positive reaction when in a certain biological environment and/or is subjected to a chemical or physical process that modifies the material's surface to form a desired substrate, in this case, for re-mineralization of dentin or enamel. Bioactive materials referred herein are those with the ability of promoting phosphate mineral (i.e. hydroxyapatite) precipitation when immersed in phosphate-rich physiological medium (i.e. saliva). A bioactive material may also bind chemically with the surrounding bone or promote cell attachment or growth.

The term "glass" refers to a non-crystalline amorphous solid having a breaking stress or surface compressive stress of 10 MPa-30 GPa at 20-40° C. Glass may or may not comprise silica ($SiO_2$).

A "composite" refers to a solid material comprising more than one phase, structure, and/or compound.

As used herein, the term "dental adhesive" refers to a composition used as a pre-treatment on a dental structure (e.g. dentin or enamel of a tooth) to adhere a "restorative material" (e.g. resin composite, ceramics, etc.).

In some embodiments, a bioactive borate glass comprises 25-60 mol %, preferably 28-55 mol %, more preferably 30-50 mol % $B_2O_3$ (borate); 15-35 mol %, preferably 17-33 mol %, more preferably 20-30 mol % CaO; 8-50 mol %, preferably 9-45 mol %, more preferably 10-40 mol % $Na_2O$; and 1-15 mol %, preferably 1.5-10 mol %, more preferably 2-5 mol % $P_2O_5$, where each mol % is in mole percents based on 100 mol % of the total composition of the borate bioactive glass which may be generated by a plurality of methods. In a preferred embodiment, a conventional "melt quench" synthesis method may be used. In this method, the borate bioactive glass may have a Ca:P molar ratio of 1:1-17:1, preferably 2:1-10:1, more preferably 3:1-7:1. The borate bioactive glass may be made by melting glass precursors such as carbonate salts, a phosphate salt, and boric acid ($H_3BO_4$) to form a glass. For example, the glass precursors, $Na_2CO_3$, $CaCO_3$, $H_3BO_4$, $NaH_2PO_4$, as well as others as needed, may be ground into powders using a mortar and pestle, or obtained as powders, and mixed to yield 20-40 g of final glass product. These powders may comprise particles having largest dimensions of 0.1-200 μm, preferably 0.5-100 μm, more preferably 1-50 μm. Preferably the mixed powder contains a ratio of the glass precursors to generate an equivalent mole percent as mentioned above. In other embodiments, different glass precursors may be used to ultimately produce equivalent compositions after melting to form a glass. For instance, $Na_2B_4O_7$ may be used in place of $H_3BO_4$, or $Na_2HPO4$ may be used in place of $NaH_2PO_4$. A person having ordinary skill in the art may be able to determine a practical amount of glass precursors to form a glass having one of the aforementioned compositions.

Some examples of preparation and treatment steps of borate glass particles in the invention are herein incorporated by reference (U.S. Pat. No. 10,624,994 to Bakry). According to some preferred embodiments, the powder mixture of glass precursors may be heated in a furnace, oven, kiln, air, Pt or Pt alloy crucible, then allowed to cool to room temperature and molded, crushed or ground to produce borate bioactive glass in the form of particles. In one embodiment, the powder mixture heated in a Pt crucible was quenched on a stainless-steel plate and pressed with another plate to obtain glass plate pieces with the thickness of 0.2-1 mm. In this embodiment, the glass particles were obtained in a porcelain mortar and further pulverized using agate planetary mill. Alternatively, a sol-gel method may be used to form the borate bioactive glass particles at lower temperatures. In addition, the particles from different glass powders may be mixed and re-melted to form the bioactive glass particles.

In one embodiment, the borate bioactive glass particles may further comprise $Ca(PO_3)_2$, $K_2O$, $TiO_2$, $CaF_2$, $Fe_2O_3$, CuO, SrO, $Bi_2O_3$, $Ce_2O_3$, $Ga_2O_3$, and/or ZnO, preferably $TiO_2$, $CaF_2$, $Fe_2O_3$, CuO, SrO, and/or ZnO, more preferably $TiO_2$, SrO, and/or ZnO. Preferably, these compounds or precursors to these compounds are added to the powder mixture before the heating and melting. It is possible that one or more of $Ca(PO_3)_2$, $K_2O$, $TiO_2$, $CaF_2$, $Fe_2O_3$, CuO, SrO, $Bi_2O_3$, $Ce_2O_3$, $Ga_2O_3$, and/or ZnO may be present in the bioactive borate glass, each at a weight percentage of 0-10 wt %, preferably 0.2-8 wt %, more preferably 0.4-6 wt %, even more preferably 0.5-3 wt %, relative to a total weight of the borate bioactive glass particles.

In a preferred embodiment, the borate glass product may be further treated with 3-6 vol % of g-methacryl-oxypropyl-trimethoxysilane (g-MPS) in acetone with 0.1-0.5 vol % of water in order to cover the exposed hydroxyl groups of the borate glass particles and to coat the hydroxyls with silane-like molecules, thus making the surface chemically inert. In this embodiment, the borate bioactive glass particles are substantially free of $Al_2O_3$, $SiO_2$ or MgO. The term "substantially free of $Al_2O_3$, $SiO_2$ or MgO" refers to the condition in which the $SiO_2$ content, the $Al_2O_3$ content, the MgO content, or all three are less than 0.5 wt %, preferably less than 0.2 wt %, more preferably less than 0.1 wt % with respect to the total weight of the borate bioactive glass. In some embodiments, borate bioactive glass being completely free of Si, Al or Mg may not be possible due to sample impurities or environmental contamination. In an alternative embodiment, the borate bioactive glass particles may comprise particles clustered together as agglomerates.

The borate bioactive glass particles disclosed herein may have overall shapes that are spherical, ellipsoidal, oblong, ovoidal, angular, rectangular, prismoidal, or some other shape. The borate bioactive glass particles may have sharp, acute, pointed, or jagged edges. In one embodiment, the borate bioactive glass particles have longest dimensions or diameters of 1-200 μm, preferably 2-100 μm, more preferably 5-40 μm. Small bioactive glass (i.e. the particles with diameters of 1-5 μm or 1-3 μm) may be used to facilitate mixing and/or to more quickly dissolve in any application solutions known in the art. Further, the present disclosure relates to a borate bioactive glass particles that are not in phosphoric acid solution or are free of any other acidic solutions.

In some embodiments, the borate bioactive glass particles may have submicron diameters, such as 100-900 nm, preferably 200-800 nm. As the average diameter of dentinal tubules is about 1 μm, particles with submicron diameters may be able to enter a dentinal tubule. The ratio of the longest dimension to the shortest dimension of the borate bioactive glass particles may be 1:1-1:10, preferably 1:1.05-1:5, more preferably 1:1.1-1:2. In one embodiment, the borate bioactive glass particles have longest dimensions within 75-125% of the average particle longest dimension, preferably within 80-120%. In one embodiment, the borate bioactive particles may have surface area to volume ratios of 15 nm$^{-1}$-50 μm$^{-1}$, preferably 0.3 μm$^{-1}$-10 μm$^{-1}$ more preferably 0.8 μm$^{-1}$-5 μm$^{-1}$ and bulk densities of 1-8 g/cm$^3$, preferably 1.2-5 g/cm$^3$, more preferably 1.5-4 g/cm$^3$. In some embodiments, the borate bioactive glass particles may have pores with diameters of 1-12 nm, preferably 1.5-8 nm, more preferably 1.8-5 nm, which may provide higher surface area to volume ratios.

To manufacture the borate bioactive glass adhesive system, which may be used to provide a micro-mechanistically enhanced adhesive platform for restorative materials to sit or bond onto dentin, a resin blend is added and mixed with the borate bioactive glass particles described above. The resin blend described herein was optimized to eliminate the disadvantage of resin modified glass-ionomer cement (RMGIC); i.e. a dental restorative material composed of a combination of glass-ionomer, composite resin and an organic acid. RMGIC is known to provide weak mechanistic strength and poor stability in moisture conditions.

In one embodiment, the silanated borate glass is incorporated with a co-monomeric resin blend at a concentration of, preferably 0.2-4 wt %, more preferably 0.5-2 wt %, relative to a total weight of the borate bioactive adhesive system. In this embodiment, the resin blend comprises 60-80% of bisphenol A diglycidyl ether dimethacrylate (Bis-GMA) or other dimethacrylate monomers, such as, 25-45% of ethylene glycol dimethacrylate with 25-45% of 10-methacryloyloxydecyl dihydrogen phosphate. In another embodiment, the adhesive system may comprise 26-30 wt % of 2-hydroxylethyl methacrylate or 26-30 wt % of N-Butyl Methacrylate. In addition, the system may further comprise 8-12 wt % of n-Butyl methacrylate in 9% of water or 9% of ethanol. Other examples of non-degradable polymers that may be added to the system include polymethylmethacrylate, polyhydroxyethylmethacrylate (HEMA), urethane dimethacrylate (UDMA), triethylene glycol dimethacrylate (TEGDMA). Of note, an adhesive system is considered as having a low viscosity setting with approximately 0.5-2% of borate bioactive glass materials.

According to another embodiment, the present disclosure relates to a method of adhering or bonding dental composites to a dentin layer or an enamel layer on a surface of a tooth. As shown in FIG. 1, the method involves applying the borate bioactive glass adhesive system onto the surface of a tooth. Then, the borate adhesive system is covered with a dental restorative composite or material of selection. The contact surface between the bioactive borate system and the treated tooth, as well as the contact between the borate adhesive system and the dental restorative composite, are hardened or cured by a plurality of adhering methods (e.g. light-activated or chemical polymerization) and by applying the required method for an effective time to cure and/or form a restored dentin layer or a restored enamel layer on the surface of the tooth. In a preferred embodiment, the effective time of light curing is about 10-40 seconds. The effective time of light curing may be adjusted accordingly based on the volume, material and/or intended purposes of the bioactive system and/or restorative materials. As used herein, "hardening" or "curing" a composition are used interchangeably and refer to polymerization and/or crosslinking reactions including, for example, photopolymerization reactions and chemical polymerization techniques.

In certain embodiments, the adhesive of the present invention is photopolymerizable, i.e., the hardenable component is photopolymerizable and the hardener includes a photoinitiator (or photoinitiator system), in which irradiation with actinic radiation initiates the polymerization (or hardening) of the adhesive. Some exemplary photoinitiators that may be incorporated into the adhesive system include 2,4,6-trimethylbenzoyl-diphenylphosphine oxide (TPO), bisacylphosphine oxide (BAPO), benzophenone (BP), camphorquinone (CQ), 9,10-phenanthrenequinone (PQ), 1-phenyl-1,2 propanedione (PPD), 9-(2,4,6-trimethylbenzoyl)-9-oxytho-9-phosphafuluorene (TMBOPF), 9-(p-toluyl)-9-oxytho-9-phosphafuluorene (TOPF), benzoyltrimethylgermane (BTMGe), dibenzoyldiethylgermane (DBDEGe), ivocerin-dibenzoyl germanium (IVO) and 7-ethoxy-4-methylcouramrin-3-yl) phenyliodo-nium hexafluoroantimonate (P3C-SB). The most preferred photoinitiator, in this embodiment, is camphorquinone, which can work by itself but becomes more efficient with further incorporation of co-initiators. The most commonly used co-initiators are ethyl-4-(dimethylamino(benzoate (EDMAB). In some embodiment, N,N-dimethyl-p-toluidine (DMPT) or 2-(N,N-dimethylamino)ethyl methacrylate (DMAEMA) may be used. Alternatively, the compositions of the adhesive system are chemically polymerizable, i.e., the compositions contain a chemically polymerizable component and a chemical initiator that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Additionally, medicaments or other therapeutic substances can be optionally added to the adhesives. Examples include, but are not limited to, fluoride sources such as tertbutyl ammonium tetrafluoroborate, whitening agents, anticaries agent, calcium sources, phosphorus sources, re-mineralizing agents (calcium phosphate compounds), enzymes, breath fresheners, anesthetics, clotting agents, acid neutralizers, chemotherapeutic agents, immune response modifiers, antimicrobial agents, antifungal agents, desensitizers, and the like. Combination of any of the above additives may also be employed. Furthermore, the adhesive system, especially at the manufacturing steps of borate bioactive glass particles, may further comprise a salt such as $KNO_3$, NaF, $SnF_2$, $SrCl_2$, and/or $CaCl_2$, preferably NaF, $SnF_2$, and/or $CaCl_2$, more preferably NaF and/or $SnF_2$. These salts may provide beneficial effects to dentin and enamel re-mineralization; for instance, fluoride from NaF or $SnF_2$ may intercalate and strengthen a hydroxyapatite lattice within or on an enamel or dentin layer. The salt may be present at a weight percentage of 0.1-10 wt %, preferably 0.2-5 wt %, more preferably 0.25-4 wt % relative to a total weight of the borate bioactive glass adhesive system.

In one embodiment, the borate bioactive glass adhesive system may be prepared immediately before applying onto a tooth. In this embodiment, the borate adhesive system may be applied directly onto the tooth surface and immediately cured by any known methods in the art (e.g. light-activated polymerization). When cured, the adhesive system may provide an adhesive surface for a restorative material (i.e. resin composite). The restorative materials may then be applied on top of the cured adhesive system and are together cured by additional light-activated polymerization. Alternatively, the borate bioactive glass adhesive system may be mixed with a selected dental restorative material or combinations of restorative materials (e.g. a resin, a ceramic, a varnish, a sealant, a bonding agent, a cement, a wax, a dental composite, a cap, a plug, a band, a dental appliance, etc.) prior to its application onto the tooth surface.

The borate bioactive glass adhesive system may be applied to a location of a tooth having an eroded or removed enamel and/or dentin layer, or having an early erosion lesion, which may be caused by chemical erosion, such as exposure to acidic compounds, beverages, or foods, or may be caused by physical abrasion, such as by filing or grinding. In one embodiment, this location to receive the borate bioactive glass adhesive system may have exposed dentinal tubules. In another embodiment, an enamel and/or dentin layer may be removed by a physical impact against a tooth, which may result in a chipped tooth. Similarly, a physical impact may result in a cracked tooth having a fissure with exposed dentinal tubules. In another embodiment, the location may be within or on a cavity or depression caused by tooth decay (i.e. dental caries). In another embodiment, the location may be located below the gum line or at a place where the gum has receded. Alternatively, the borate bioactive glass adhesive system may be applied to a surface of a tooth that is not enamel or dentin, for example, the cementum. As non-limiting examples, the tooth may be an incisor, a cuspid, a bicuspid, a premolar, or a molar, and may be a primary tooth or a permanent tooth. The borate bioactive glass adhesive system may be placed by means of a dental spatula, an elevator, an applicator, or a brush, or may be applied by extruding from a tube or syringe. In one embodiment, where the borate bioactive glass adhesive system is applied by an applicator, it may be applied by a Microbrush applicator. In one embodiment, the borate bioactive glass adhesive system may be applied to just fill a cavity or depression on the surface of the tooth, so that the borate bioactive glass adhesive system lies flush against the surface of the tooth. In other embodiments, an amount of borate glass adhesive system may be applied that is less than that required for a flush surface (thus leaving a concave surface or a surface within the tooth), or the amount of borate bioactive glass adhesive system may be greater than that required for a flush surface (thus leaving a convex shape). The ratio of the applied volume of the borate bioactive glass adhesive system to the volume of the tooth above the gum line may be 1:200-1:1, preferably 1:50-1:2, more preferably 1:40-1:5. In an alternative embodiment, a single volume of borate bioactive glass adhesive system may not be placed just on a single tooth, but on two or more teeth as a contiguous volume, such as filling a gap between two teeth.

The bioactive borate glass adhesive system may potentially be used for non-dental bone structures as well. However, tooth restoration strategies and the use of borate adhesive system for such strategies are greatly different from those for non-dental bones. Since bones can often regenerate, materials for bone repair should be selected based on their abilities in slow degradation to components that may be used for tissue renewal and/or safe removal afterward. However, the composite materials in the tooth restoration should provide permanency, as the natural repair in the tooth is limited. Although a non-degradable polymer or material is preferred for the tooth restoration purposes, calcium phosphate leaching out from the set material may also be preferred so long as there is no decline in material strength as well as in volume.

Since dentin is covered in a hard outer layer of calcium phosphate mineral containing enamel, which is the hardest substance in the human body, when the enamel is cracked, chipped, or decayed, the dentin is exposed to acid and bacteria build up. While bones are mostly made of collagen, dentin is composed of 45% of mineral hydroxyapatite, 33% of organic material and 22% of water. The bioactive borate glass composition and adhesive system can further provide a method of treating dentin hypersensitivity comprising: applying at least one surface of a tooth sample having at least one indication of dentin hypersensitivity with a formulation including any of the disclosed compositions.

In one embodiment, before applying the borate bioactive adhesive system, the surface of the tooth may be cleaned or prepared by air jet, water jet, polishing, brushing, drilling, scraping, grinding, acid etching, or de-mineralizing. Acid etching or de-mineralizing may be done with a solution comprising citric acid, phosphoric acid, EDTA, hydrochloric acid, acetic acid, or some other inorganic acid, organic acid, or chelating agent. In one embodiment, preparation of the surface by drilling, scraping, grinding, acid etching, or de-mineralizing may increase the surface roughness and provide additional crevices for a layer of calcium phosphate to deposit and anchor. The surface roughness on the prepared tooth, for example, within a 10 µm×10 µm region, may possess an Ra roughness value of 0.10-0.30 µm, preferably 0.12-0.25 µm. However, in some embodiments, a tooth may already have an equivalent surface roughness by erosion and may not need additional abrasion or etching.

For storage, the borate bioactive glass adhesive system may be formed in advance and then stored for 1-12 months, preferably 2-8 months, more preferably 3-6 months in an airtight container and stored at room temperature, or in a refrigerator or freezer. In another embodiment, a mixture of the borate bioactive glass particles, resin blend, photoinitiator and co-initiator may be formed in advance and stored. In another embodiment, each component may be prepared separately and, within 20 minutes or 10 minutes of application to a tooth, the mixture may be made to form the borate bioactive glass adhesive system.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided it is understood that each intervening value, to the tenth of the unit of the lower limit unless the context clearly dictates otherwise, between the upper and lower limit of that range and any other stated or intervening value in that state range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only" and the like in connection with the recitation of claim elements or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the invention has been described in terms of its preferred embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

Example 1

Method of Manufacturing the Borate Glass

Borate-based bioactive glass with the composition of 24.4 $Na_2O$-26.9 $CaO$-2.6 $P_2O_5$-46.1 $B_2O_3$ in mol % was prepared by a conventional melt-quenching method. The reagent grade $Na_2CO_3$, $CaCO_3$, $H_3BO_4$ and $NaH_2PO_4 \cdot 2H_2O$ were mixed as the glass yield of 30 g by using an aluminum mortar. The resulting mixture was put in a Pt crucible and then heated in an electric furnace in air for 1 h at 1450° C. The melt was quenched by pouring it on a stainless-steel plate and pressed with another plate to obtain glass plate pieces with the thickness of 0.2-1 mm. Glass particles were obtained by crushing the glass using a porcelain mortar and pestle. The glasses were pulverized (less than 90 micron) using agate planetary mill and were treated with g-methacryloxypropyltrimethoxysilane (g-MPS) (Aldrich Chemical Co., Milwaukee, Wis.) in acetone.

Silanization of the Glass Particles

The glass particles were dried at 100° C. for 2 h at atmospheric pressure before the reaction. For the silanation process 5 g of glass particles were agitated for 2 h in acetone with 0.3 vol % of water and 4 vol % of g-MPS (of total solvent volume). Sonicated for 20 min and additionally agitated for 2 h. The silanated particles were separated using a centrifuge. Washed three times with pure acetone, Dried at room temperature overnight and then in the oven at 100 C for 2 h.

Synthesis of Borate Resin Bonding Agent

The silanated Borate glass was incorporated at different concentration (0.5 wt %, 1.0 wt % and 2 wt %) into a co-monomers resin blend (DA) consisting of 70 wt % bisphenol A diglycidyl ether dimethacrylate (Bis-GMA) or (35% Ethylene glycol dimethacrylate and 35% 10-Methacryloyloxydecyl dihydrogen phosphate) (28.75 wt % 2-hydroxylethyl methacrylate) or (28.75 wt %. N-Butyl Methacrylate) or (10% n-Butyl methacrylate wt %, 9% water, 9% ethanol) or wt % ethyl N,N-dimethyl-4-aminobenzoate (EDMAB) as an co-initiator. 0.25 wt % camphorquinone (CQ) was used as an initiator. The whole mixture was placed in opaque bottles and placed in ultrasonic bath for two minutes.

Example 2

Dentin Specimens' Preparation

Figure 2A:
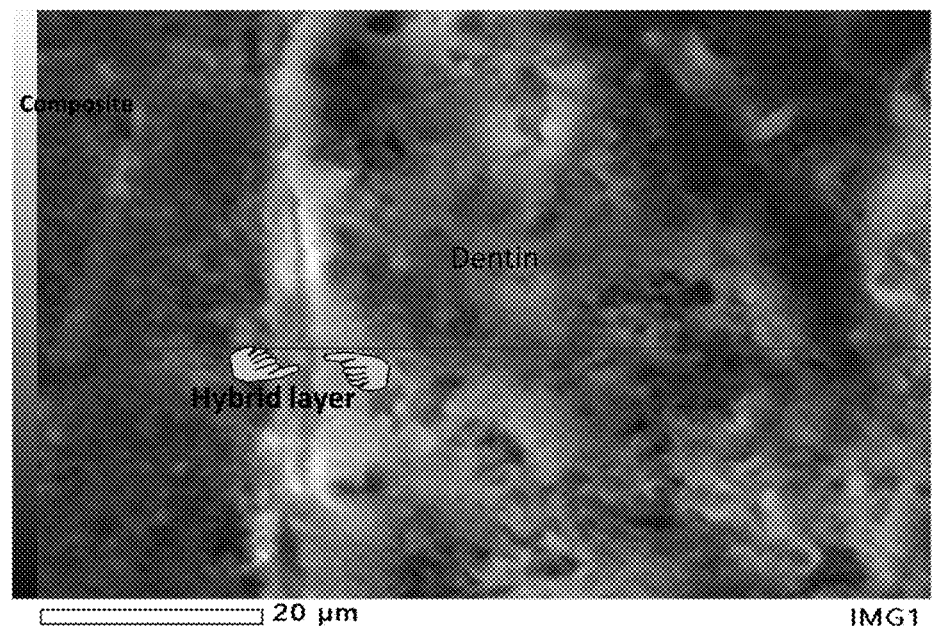
FIG. 2A is an FE-SEM image of a tooth cross-section having an interaction layer of calcium phosphate deposited on the dentin surface in the presence of borate bioactive particles and resinous components.
Figure 2B:
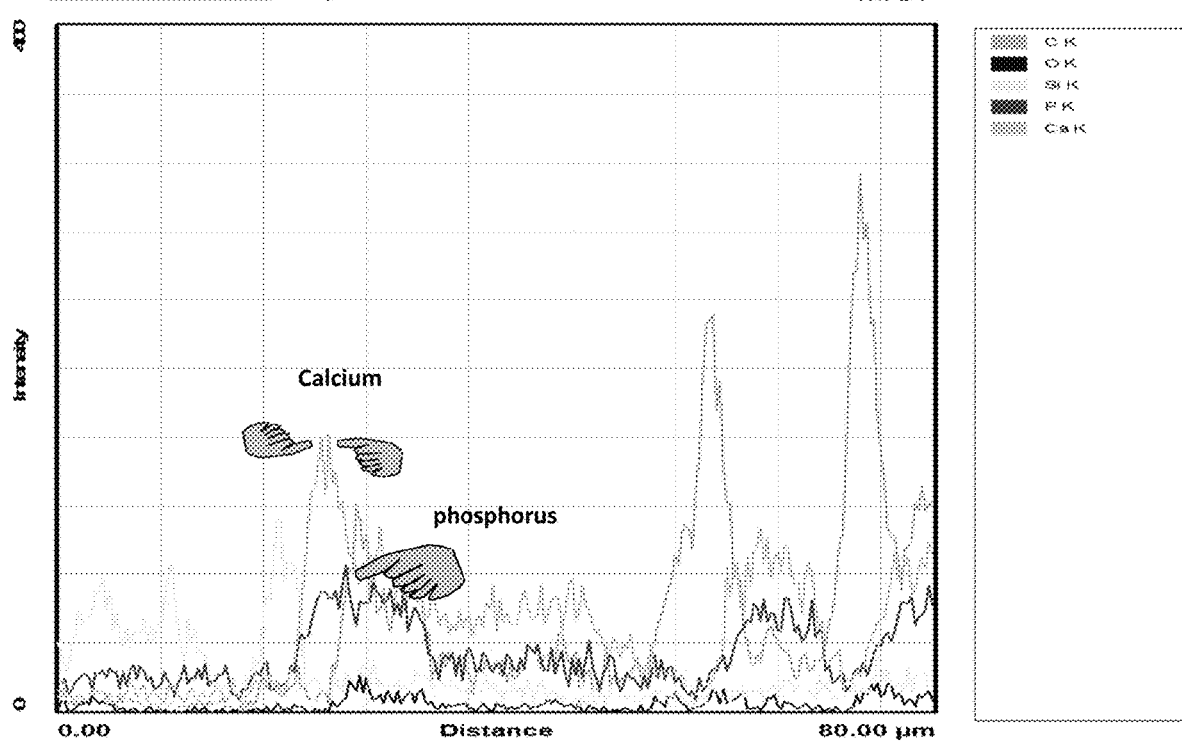
FIG. 2B is an EDS-line scan profile corresponding with the dotted line on the tooth cross-section in FIG. 2A.
Figure 3A:
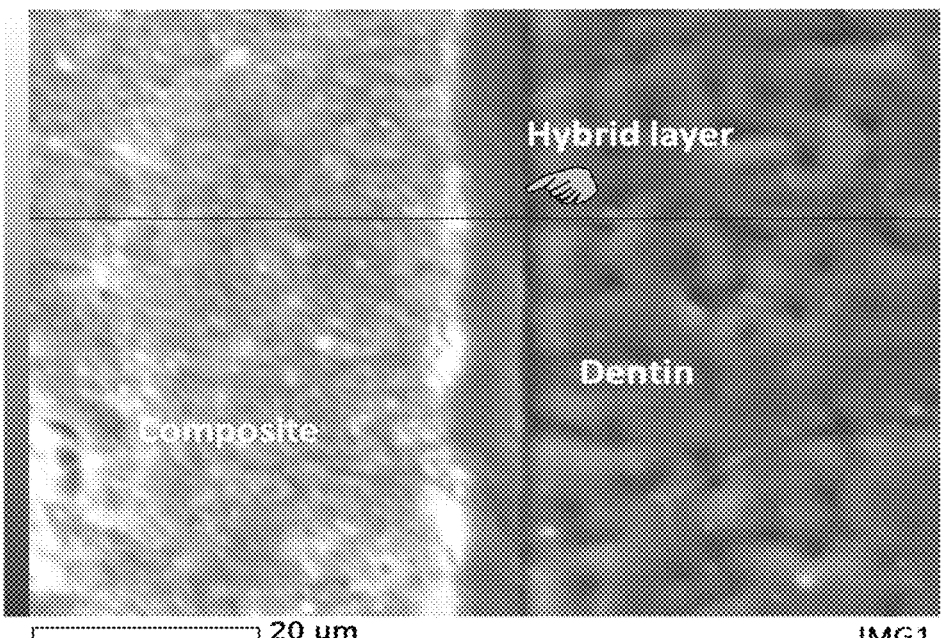
FIG. 3A is an FE-SEM image of a tooth cross-section having an interaction layer of calcium phosphate deposited on the dentin surface in the presence of resinous components not containing borate bioactive particles.
Figure 3B:
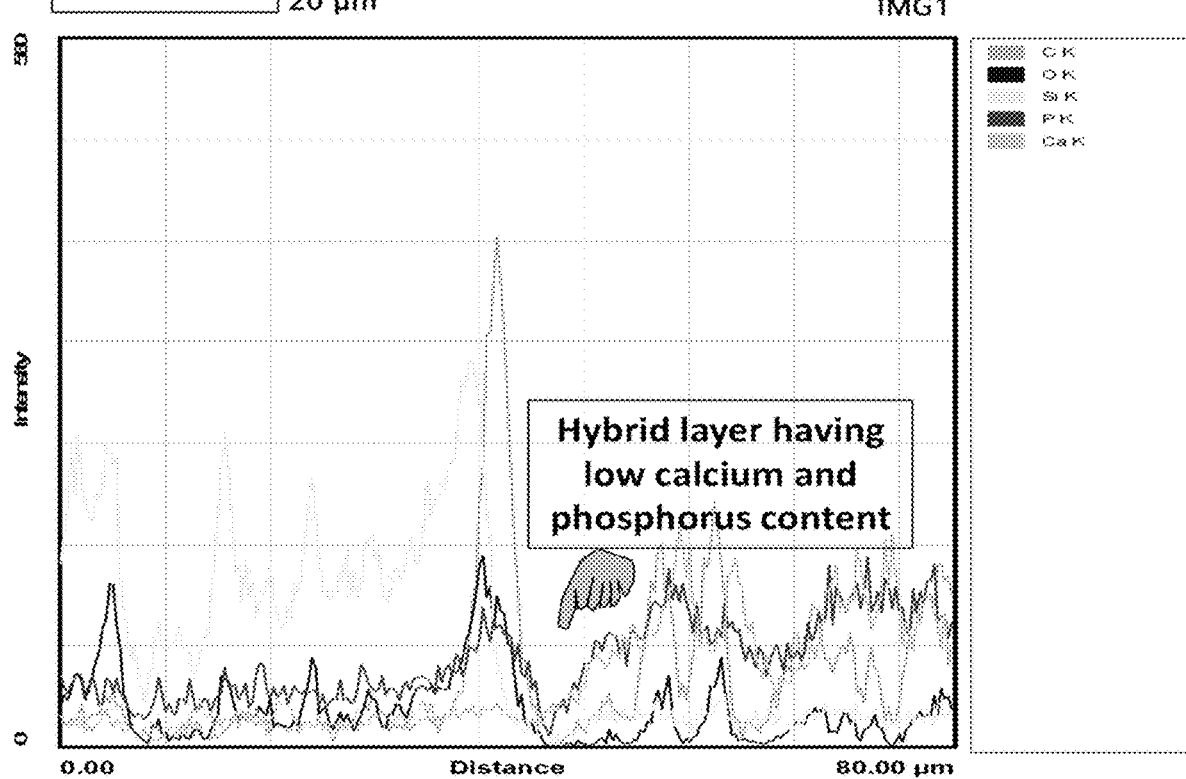
FIG. 3B is an EDS-line scan profile corresponding with the dotted line on the tooth cross-section in FIG. 3A.

Freshly extracted 10 non-carious third molars were used. Sections of teeth exposed in their mid-coronal dentin surface, which were ground flat to expose dentin surfaces utilizing 600 grit sandpaper under water irrigation to obtain a standardized smear layer, were prepared. The specimens were assigned to two different groups n=10. Group I (FIG. 2) contained borate particles while Group II (FIG. 3) had the same resinous components but free from borate bioactive particles.

Example 3

Borate Glass Adhesive System Application

The enamel and dentin surfaces were etched with 37% phosphoric acid for 15 seconds followed by washing by water jet and drying by compressed dry air for 10 seconds. The borate glass adhesive system was applied onto the dentin surfaces and then light cured for 10 seconds. Composite light curing posterior filling was applied onto the dentin surface followed by light curing for 30 seconds. The specimens were cross-cut by isomet and placed in sodium hypochlorite for 60 minutes followed by immersion in artificial saliva for 24 hours.

FE-SEM/EDS Interface Examination

The specimens were stored in de-ionized water for 24 hrs, then sectioned perpendicular to the interface to give 1.5-mm-thick slabs. The cut surfaces were polished, etched, gold-coated, and then examined by FE-SEM/EDS. Line scans were done across the adhesive system-tooth interface to examine the following elements: phosphate, calcium, carbon and silica. Specimens of groups I and II showed good adaptation of both bonding agents to the dentin surface with no signs of debonding or cracks at the interface.

The specimens of group I showed that the hybrid layer interface was heavily infiltrated by calcium and phosphate deposits, however specimens of group II showed absence of any calcium or phosphate within the resin-dentin interface. The results showed that the addition of borate glass particles 2% borate glass to a resin blend created a bonding agent capable of releasing a high content of calcium and phosphate at the resin dentin interface.

The dentin surfaces that were bonded to the bonding resins were etched with phosphoric acid for 15 seconds and thus were free from any smear layers or plugs and the inorganic content of dentin at these areas should be depleted when compared to the inorganic content of the rest of the sound dentin. In the current experiment doping of the bonding resin with 2% borate glass released high content of calcium and phosphate that were higher than the calcium and phosphate content of the sound dentin.

The current experiment included complete deprotinization of any hydroxyapatite-denuded collagen at the hybrid layer to avoid any possible remineralization for the collagen at this area induced by storage of the specimens in re-mineralizing solution, which demonstrated that the borate glass bonding agents bioactive re-mineralizing action can be induced irrelevant of the existence of any collagenous or organic matrix.

The borate glass is known for its well documented bioactivity and its ability to release high content of calcium when it is in contact with simulated body fluids. The capability of the borate glass in inducing an interaction layer rich in calcium and phosphate and recommended its possible use as a desensitizing agent is known in the art. Previously utilized borate particles mixed with a diluted phosphoric acid aqueous solution was different from the presented invention in that the particle mixture was without any resinous components.

Figure 4:
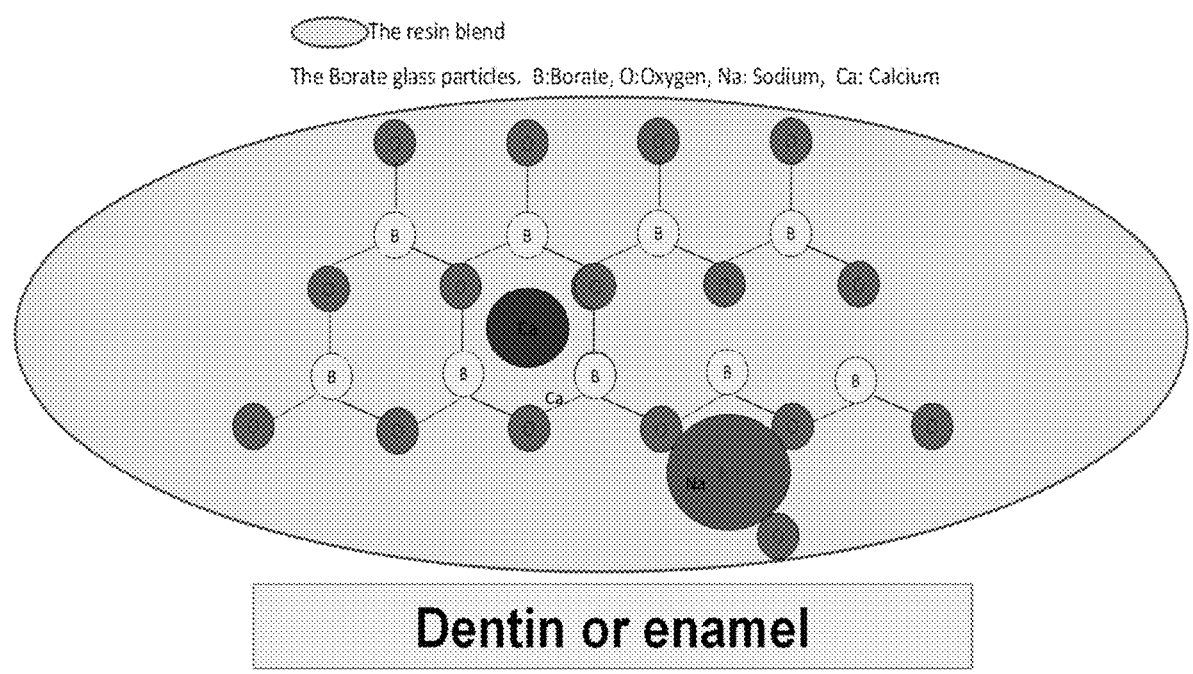
FIG. 4 is a representative diagram showing a borate bioactive glass particle on a surface of dentin or enamel.
Figure 5:
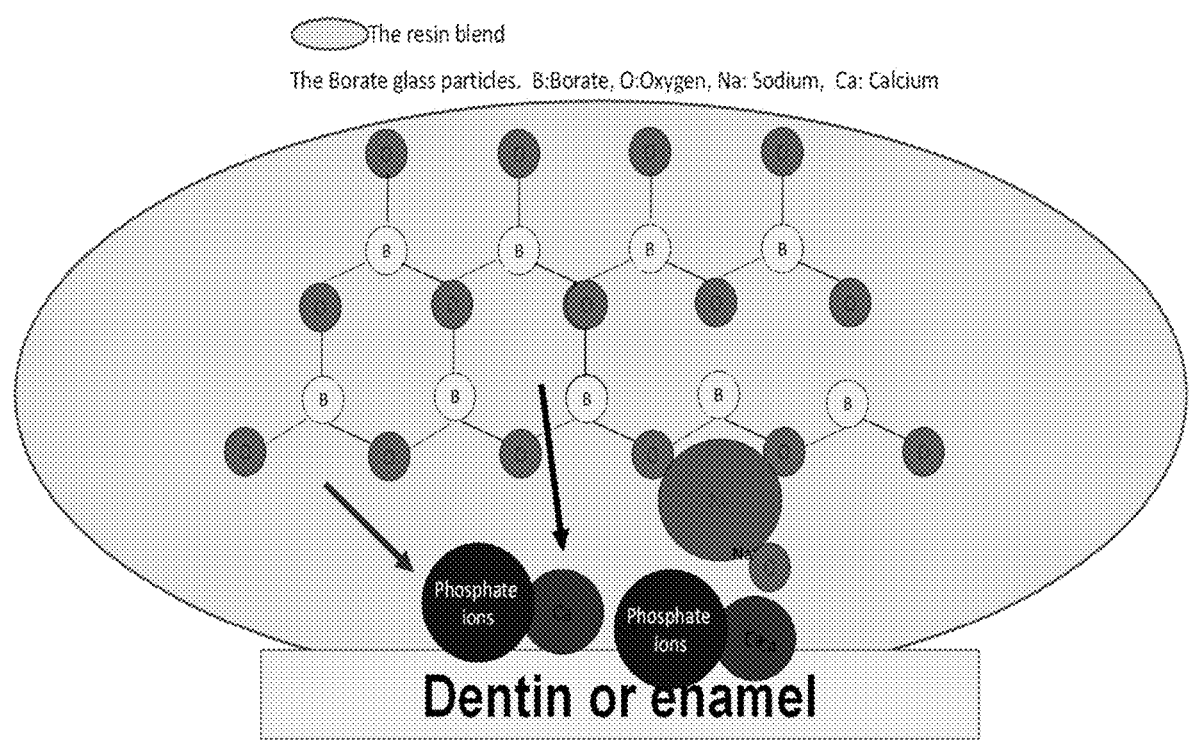
FIG. 5 is a representative diagram showing potassium and calcium ions release and further depositing onto the surface of dentin or enamel.

It is suggested that the mechanism of action of the borate bioactive bonding agent is induced from the bioactive glass and partially from the resinous part of the bonding agent because the interface between the bonding agent and the dentin was heavily infiltrated by calcium and phosphate (FIG. 4 and FIG. 5). It may be suggested that the bonding agent when applied onto the etched dentin infiltrated the demineralized collagen network of the dentin to form a hybrid layer. The thickness of the hybrid layer in the current experiment was approximately 2 µm and was evident by its chemical characterization by EDS. The extremely micron sized resin-collagen interface diminished the resinous coating of the borate bioactive particles that are dispersed in the bonding bioactive and caused its exposure to the storage re-mineralizing solution (simulating the exposure of the bonded interfaces to saliva in oral cavity) triggering the start of bioactivity cycles of few borate glass particles at the interface region which may interact by phosphorus of the storage media and phosphorus of the 10MDP component to form calcium phosphate complexes at the interface area which were detected by the EDS analysis.

The remaining dispersed borate bioactive particles in the borate bioactive bonding agent did not undergo any bioactive reaction of releasing a detectable calcium release as was evidence by the EDS analysis which may be attributed to the presence of ample resin coating surrounding the silanized borate bioactive glass which insulated the borate particle from becoming in contact with the storage solution and stopped its bioactivity.

The current hypothesis suggest that any significant loss of the resinous matrix of the borate bioactive glass bonding agent due to aging of using this material inside patients' mouth may expose the embedded (self healing) bioactive glass particles to become in contact with the storage media or saliva and trigger the bioactive cycle of forming the calcium-phosphate rich compounds to self-heal the defective part of the resin matrix and stop its further degradation. Moreover, the high calcium and phosphate content of the hybrid layer formed at the interface may serve as an effective barrier against the low pH acidic attacks launched by the bacterial biofilms at the resin-dentin interface which may lead to increase the service of the bonded restoration inside the oral cavity of patients.

In FIG. 5, the borate bioactive bonding agent could actively release detectable levels of calcium which formed calcium phosphate rich complexes at the hybrid layer interface (Dentin-resin interface), suggesting the increase of the acid resistance of this area which was considered as the most vulnerable area for failure due to its poor calcium and phosphate content.

What is claimed is:

1. A bioactive borate adhesive system comprising:
   bioactive borate glass particles, wherein the particles are at a concentration of 0.5-2.0 wt %;
   a co-monomer resin blend, wherein the resin blend comprises 60-80 wt % of bisphenol A diglycidyl ether dimethacrylate (Bis-GMA);
   a photoinitiator; and
   a co-initiator.

2. The adhesive system of claim 1, wherein the bioactive borate glass particles comprise 10-40 mol % $Na_2O$, 20-30 mol % CaO, 1-5 mol % $P_2O_5$, and 30-50 mol % $B_2O_3$.

3. The adhesive system of claim 1, wherein the resin blend further comprises a mixture of triethylene glycol dimethacrylate (TEGDMA) and 10-Methacryloyloxydecyl dihydrogen phosphate in a 1:1 ratio.

4. The adhesive system of claim 1, wherein the photoinitiator is selected from 0.15-0.3 wt % of camphorquinone (CQ), phenylpropanedione (PPD) or 2,4,6, trimethylbenzoyl-diphenylphosphine oxide (TPO).

5. The adhesive system of claim 1, wherein the co-initiator is selected from 0.5-1.5 wt % of N,N-dimethyl-p-toluidine (DMPT), 2-(N,N-dimethylamino)ethyl methacrylate (DMAEMA) or ethyl N,N-dimethyl-4-aminobenzoate (EDMAB).

6. The adhesive system of claim 1, wherein the bioactive borate glass particles are silanized.

7. The adhesive system of claim 1, wherein the system is substantially free of phosphoric acid.

8. The adhesive system of claim 1, wherein the system does not include $Al_2O_3$, $SiO_2$, or mixtures thereof.

9. A method of bonding dental restorative material on a tooth structure, comprising:
   applying the adhesive system of claim 1 onto an exposed surface of a tooth;
   curing with light for an effective amount of time to adhere the adhesive system of claim 1 onto the exposed surface of the tooth, wherein the exposed surface is dentin or enamel;
   applying one or more dental restorative materials on top of the cured adhesive system; and
   curing with light for an effective amount of time to form restoring dentin or enamel layers.

10. A method of bonding dental restorative material on a tooth structure, comprising:
    mixing or attaching one or more dental restorative materials with the adhesive system of claim 1;
    applying the mixture containing one or more dental restorative materials and the adhesive system onto an exposed surface of a tooth; and
    curing with light for an effective amount of time to form a restoring dentin or enamel layer.

11. The method of claim 10, wherein the dental restorative material is selected from the group consisting of a resin, a ceramic, a varnish, a sealant, a bonding agent, a cement, a wax, a dental composite, a cap, a plug, a band, and a dental appliance.

12. The method of claim 10, wherein the method further comprises an enamel etching step with 30-50% of phosphoric acid prior to the application of the adhesive system and the dental restorative materials on the exposed surface of the tooth.

13. The method of claim 10, wherein the adhesive system releases calcium and phosphate ions to a hybrid layer when exposed to saliva.

14. The method of claim 13, wherein the calcium and phosphate ions form a hydroxyapatite layer on the surface of dentin or enamel to re-mineralize a tooth.

15. The method of claim 10, wherein the exposed surface of a tooth has exposed dentinal tubules or is within a dental cavity.

16. The method of claim 10, wherein the effective time to form a restoring dentin or enamel layer is about 10-40 seconds.

* * * * *